United States Patent [19]

Boudakian et al.

[11] Patent Number: 4,927,940

[45] Date of Patent: May 22, 1990

[54] PROCESS FOR LOW CHLORIDE 1,2,4-TRIAZOL-5-ONE

[75] Inventors: Max M. Boudakian, Pittsford; Delmer A. Fidler, Rochester, both of N.Y.

[73] Assignee: Olin Corporation, Cheshire, Conn.

[21] Appl. No.: 345,376

[22] Filed: May 1, 1989

[51] Int. Cl.$^5$ .......................................... C07D 249/12
[52] U.S. Cl. .................................................. 548/263.2
[58] Field of Search ........................................ 548/263

[56] References Cited

U.S. PATENT DOCUMENTS

| | | | |
|---|---|---|---|
| 2,763,661 | 9/1956 | Grundmann et al. | 548/263 |
| 3,890,342 | 6/1975 | Krenzer | 548/263 |
| 3,922,162 | 11/1975 | Krenzer | 71/92 |
| 4,467,098 | 8/1984 | Koch et al. | 548/263 |
| 4,482,738 | 11/1984 | Rothgery | 564/37 |

FOREIGN PATENT DOCUMENTS 0210881 2/1987 European Pat. Off. .

OTHER PUBLICATIONS

Chem. Abst. 54;22602: Ann. Chim. (Rome), 49, 1649–67 (1959), "Reactions Between Organic Nitrogen Compounds and Ethyl Orthoformates, I. Hydrazides and Derivatives".

Chemische Berichte, vol. 98–II, "Synthesen und Reaktionen von 4–Amino–1,2,4–Triazolonen–(5)", pp. 3025–3033, 1965.

Chem. Abst. 62;14437: Ann. Chem., 682, pp. 123–135 (1965)(Germany), "1,2,4–Triazol–5–Ones, V. Effect of Substituents on the Rate of Hydrolysis in Half–Concentrated Sulfuric Acid".

Chem. Abst. 65;705: Khim. Geterotsikl. Soedin., Akad. Nauk Latv. SSR, 1966 (1), pp. 110–116 (Russian), "$\Delta^5$–1,2,4–Triazolin–3–One and Its Nitro and Amino Derivatives".

Chem. Abst. 100;34468: Ann. Univ. Mariae Curie-Sklodowska, Sect. AA, Chem, 1979 (Publ. 1982), 34, pp. 163–168 (Polish), "Trifomylaminomethane, II. Reaction With Thiosemicarbazide, Semicarbazide, and Aminoguanidine".

Chemical Reviews, "Formylating Agents" (G. A. Olah et al), American Chemical Society, vol. 87, No. 4, Aug. 1987, pp. 671–686.

Primary Examiner—Glennon H. Hollrah
Assistant Examiner—Patricia L. Morris
Attorney, Agent, or Firm—James B. Haglind; Paul Weinstein

[57] ABSTRACT

A process for producing 1,2,4-triazol-5-one reacts an aqueous hydrazine solution with urea to form a reaction mixture of semicarbazide and ammonia, the reaction mixture is concentrated and an aqueous solution of a mineral acid added to form a slurry of a salt of semicarbazide. A formic acid compound is admixed with the slurry, and the slurry heated to produce 1,2,4-triazol-5-one. The novel process results in the production of a semicarbazide salt in situ and eliminates a number of process steps required in processes of the prior art.

15 Claims, No Drawings

PROCESS FOR LOW CHLORIDE 1,2,4-TRIAZOL-5-ONE

This invention relates to a process for the production of triazolone compounds. More particularly, the invention relates to a process for the production of 1,2,4-triazol-5-one from semicarbazide compounds.

1,2,4-Triazol-5-one (or its tautomeric form; 5-hydroxy-1H-1,2,4-triazole) is a known compound useful as an intermediate in the production of explosives and in the synthesis of dyestuffs.

The preparation of 1,2,4-triazol-5-one has been reported by a number of investigators. C. Runti et al [Ann. Chim. (Rome) 49, 1649–1667, 1959: Chem. Abstracts 54,22602K (1960)] refluxed semicarbazide.HCl with ethyl orthoformate for one hour, the reaction mixture cooled, filtered, and crystallized from ethanol to give 1,2,4-triazol-5-one.

C. F. Kroeger et al prepared 4-amino-1,2,4-triazol-5-one by heating carbohydrazide and ethyl orthoformate on a water bath. The amino derivative was deaminated by treatment with $NaNO_2$ in HCl and neutralized with NaOH [Chem. Ber. 98 (9) 3025–3033 (1965); Chem. Abstracts 63,16339g (1965)].

1,2,4-Triazol-5-one was prepared by G. I. Chipen et al by several methods including the reaction of formic acid with acetone semicarbazone and with semicarbazide.HCl, the latter method being considered optimal. Semicarbazide.HCl and 85 percent formic acid were boiled for eight hours and kept for twelve hours at 0° C. to prepare 1,2,4-triazol-5-one. [Khim. Geterotsikl. Soed. 2 (1) 110–116 (1966); Chem. Abstracts 65,705b (1966)].

M. Dobosz prepared 1,2,4-triazol-5-one by the reaction of triformylaminomethane with semicarbazide or its hydrochloride as reported in Ann. Univ. Mariae Curie-Sklodowska, Sect. AA: Chem. 34, 163 (1979), Chem. Abstracts 100 34468, (1984).

A preferred reactant in known processes for 1,2,4-triazol-5-one is a salt of semicarbazide such as semicarbazide hydrochloride. These salts have been prepared by a variety of synthesis routes. One preparation method involves reacting carbon monoxide with hydrazine at superatmospheric pressures, at temperatures in the range from 0° C. to 200° C., and in the presence of a catalytic amount of a metal carbonyl to obtain semicarbazide which is acidified to yield the desired salt. See U.S. Patent Reissue No. 24,526, Aug. 26, 1958, to H. J. Sampson, Jr.

Another method involves reacting nitrourea with hydrogen in the presence of a hydrogenation catalyst, hydrochloric acid and an inert solubilizing agent to produce semicarbazide hydrochloride as taught in U.S. Pat. No. 2,749,217, which issued to A. J. Deutschman, Jr. on June 5, 1956.

The reaction of an aqueous solution of hydrazine with a large stoichiometric excess of urea is described by T. Takacsik et al in Romanian Patent No. 51,012, published June 5, 1968. In this process, hydrazine and an excess of urea are refluxed and additional urea is added to the mixture periodically. The reaction mixture is cooled, treated with cold water, and after separation of a precipitate formed, treated with a concentrated mineral acid.

One commercial route to semicarbazide hydrochloride involves the reaction of hydrazine hydrate (64 percent by weight hydrazine) with urea. At the end of the reaction, the water and unreacted hydrazine from the hydrazine solution is stripped. The reaction mixture is then digested in methanol followed by filtering off methanol-insoluble by-products (e.g. hydrazodicarbonamide). The remaining filtrate is acidified with aqueous hydrochloric acid to precipitate semicarbazide hydrochloride which is then recovered.

A preferred process for semicarbazide hydrochloride reacts an aqueous hydrazine solution at a temperature of 80° C. to 130° C. and at a mole ratio of hydrazine to urea from 0.9:1 to 1.2:1 (U.S. Pat. No. 4,482,738, issued Nov. 13, 1984 to E. F. Rothgery). The reaction mixture formed is concentrated by removing substantially all of the water, ammonia, and unreacted hydrazine, and a sufficient amount of an alcohol added to dissolve the semicarbazide and to precipitate alcohol-insoluble by-products. After separating the by-products, the alcohol solution of semicarbazide is reacted with anhydrous hydrogen chloride to precipitate semicarbazide hydrochloride.

This process, while producing semicarbazide hydrochloride in good yields, is a multi-step procedure which requires the use of an alcohol such as methanol as an extractant and its subsequent recovery, costly gaseous hydrogen chloride as a reagent, and the separation recovery, purification and drying of semicarbazide hydrochloride.

The preparations recorded in the prior art for 1,2,4-triazol-5-one result in low yields or, where semicarbazide.HCl is a reactant, the product contains high concentrations of chloride ions. In an important application, the triazolone compound is nitrated to produce 3-nitro-1,2,4-triazol-5-one which is used in cast explosive compositions. It is known that the presence of high chloride concentrations in castable explosives stored, for example, in metal casings results in increased corrosion of the casings and increased gas formation.

In addition, 1,2,4-triazol-5-one having high concentrations of chloride ion can undergo undesired chemical reactions. For example, Kroeger et al (op. cit.) found that when 3-nitro-1,2,4-triazol-5-one was heated with hydrochloric acid, chlorodenitration resulted and 3-chloro-1,2,4-triazol-5-one was formed in 87 percent yields.

Now it has been found that 1,2,4-triazol-5-one can be produced in a simplified process with good yields and having a low concentration of chloride ion.

The process for producing 1,2,4-triazol-5-one comprises reacting aqueous hydrazine with urea to form a reaction mixture of semicarbazide and ammonia, concentrating the reaction mixture, adding a solution of mineral acid to the reaction mixture to form a slurry of a salt of semicarbazide, admixing a formic acid compound with the slurry, and heating the slurry to produce 1,2,4-triazol-5-one.

The initial reactants for the process of the present invention are widely available chemicals. Urea is a commercially available commodity chemical. Hydrazine is also commonly available in the form of hydrazine hydrate (an aqueous solution containing 1 mole hydrazine and 1 mole $H_2O$ or 64 percent by weight hydrazine). Other aqueous solutions (e.g., solutions containing from about 95 percent to about 5 percent by weight hydrazine) are readily attainable. Hydrazine hydrate is the preferred source of hydrazine for this process.

The mole ratio of hydrazine to urea used is from about 0.9:1 to about 1.2:1. Low yields of semicarbazide are obtained if a significant excess of hydrazine is employed, and the formation of the by-product, hydrazodicarbonamide, is favored with a significant excess of urea. It is more preferred to employ a hydrazine to urea mole ratio form about 0.95:1 to about 1.1:1.

The temperature for the reaction of hydrazine with urea should be from about 80° C. to about 130° C. in order to achieve a reasonable reaction rate. The reaction rate appears to slow down significantly below about 80° C. Above about 130° C., degradation reactions are initiated which lower the yield. Preferably, the reaction should be carried to about 100° C. to about 120° C. The reaction time is directly dependent upon the reaction temperature and with higher temperatures a shorter time is needed. The reaction does not require the use of either sub- or superatmospheric pressures during the reaction. It is preferred to use atmospheric pressure reactors of conventional construction. It should be noted that ammonia is evolved as a by-product during the reaction and minute amounts of ammonia may be still present at the end of the reaction.

After the reaction is complete, it is desirable to concentrate the reaction mixture. This concentration removes water, excess hydrazine and ammonia present in the reaction mixture. Any conventional means of concentration may be employed, with vacuum distillation being preferred.

Following the concentration of the reaction mixture, it may be desirable to remove impurities such as hydrazodicarbonamide from the reaction mixture. This can be accomplished, for example, by extracting the semicarbazide free base produced in the process with water and separating insoluble materials.

Upon completion of the concentration step, a mineral acid such as hydrochloric acid, sulfuric acid, or mixtures thereof, is added to the concentrated reaction mixture to produce a salt of semicarbazide i.e. semicarbazide hydrochloride or semicarbazide sulfate or bisulfate, or mixtures thereof.

The semicarbazide salt is then reacted with formic acid compound in the novel process of the present invention which results in the ring-forming or cyclization reaction required to produce the 1,2,4-triazol-5-one.

Suitable formic acid compounds include those represented by the formula:

$$HCZ \qquad (I)$$

wherein
Z represents $O_2H$, $O_2R''$, $(OR'')_3$, $O_2M$, $ONH_2$, or $(NHCHO)_3$, in which
R'' represents a lower alkyl group, and
M represents an alkali metal.

Suitable formic acid compounds represented by Formula I include formic acid, formic acid esters ($O_2R''$) or orthoformic acid esters $(OR'')_3$ having 1 to about 6 carbon atoms, alkali metal formates such as sodium formate or potassium formate, formamide, and triformylaminomethane.

Preferred are formic acid compounds represented by Formula I wherein Z represents $O_2H$, $O_2R''$, or $(OR'')_3$ in which R'' represents a lower alkyl group having from 1 to about 3 carbon atoms. Examples of these preferred embodiments include formic acid, methyl orthoformate, and ethyl orthoformate.

To conduct the process of the invention, the semicarbazide hydrochloride and the formic acid compound are heated at temperatures up to about reflux to produce a reaction mixture containing 1,2,4-triazol-5-one. While the reaction is preferably conducted at about atmospheric pressure, superatmospheric pressures may be employed if desired.

During the cyclization or ring-forming step of the process, a gas such as hydrogen chloride may be evolved which can be fed, for example, to a scrubber containing a solution of an alkaline compound including a hydroxide or carbonate.

After the reaction is complete, the temperature is increased to strip off the formic acid compound. Where formic acid is the formic acid compound, an azeotrope with water is formed.

In the novel process of the present invention, one or more liquors containing solubilized triazolone product, produced at subsequent steps or stages of the process, are recycled to the reaction mixture. The liquors may be recycled directly to the reactor from the process step in which they are generated or they may be returned to one or more storage vessels in which they may be mixed and after mixing added to the reaction mixture.

Where semicarbazide hydrochloride is the salt employed in the process of the present invention, distilling or stripping the formylating agent in the presence of the chloride liquors results, surprisingly, in a further reduction of the chloride-ion concentration of the product, an increase in product yields by recovery of solubilized triazolone product.

In addition, the process permits a substantial reduction in the number of effluent streams to be disposed of as well as a significant reduction in effluent treatment steps.

Following stripping of the formic acid compound, the reaction mixture is cooled to crystallize the 1,2,4-triazol-5-one present. The crystals, slurried in a mother liquor which contains chloride ions, are separated from the mother liquor. The mother liquor is suitable for recycle to the formylating agent stripping step in place of water which is used in processes of the prior art.

Recrystallization of the 1,2,4-triazol-5-one crystals is carried out, for example, by slurrying the crystals in water, heating the slurry to solubilize the 1,2,4-triazol-5-one crystals, and cooling the slurry to form crystals of 1,2,4-triazol-5-one of a higher purity. The supernatant liquor which contains chloride ions and solubilized triazolone is removed and may be recycled to the formic acid compound stripping step. The recrystallization step may be repeated if desired.

1,2,4-Triazol-5-one crystals produced by the novel process of the invention are highly pure and have reduced chloride ion concentration at levels which will not result in corrosion when used in castable explosives such as 3-nitro-1,2,4-triazol-5-one. These crystals may be dried or further reacted to produce the desired derivative.

The novel process of the present invention permits a reduction in the number of process steps as the semicarbazide compound is produced in situ and its isolation and separation using an alcohol, and purification and drying is not required. In contrast, the processes of the prior art employ pre-formed semicarbazide compounds as a reagent. In addition, higher yields of 1,2,4-triazol-5-one are achieved and crystals of higher purity obtained as the chloride-ion concentration is significantly reduced. Further, it provides the opportunity for potential infinite recycle of the chloride liquors containing solubilized triazolone product. Still further, the process, which can be operated continuously, generates effluents which after neutralization can be readily disposed of in public waterways.

The following examples further illustrate the novel process of the invention without any intention of being limited thereby. All parts and percentages are by weight unless otherwise indicated.

EXAMPLE 1

A mixture consisting of 64 percent hydrazine (209 grams, 4.18 moles) and urea (250 grams, 4.17 moles) was heated at 113° C. for two hours. Ammonia was liberated during this step. Unreacted hydrazine was then removed under vacuum (32° C.–102° C./28–52 mm.). The distillate (weight 142.5 grams) contained 7.4 percent hydrazine (0.33 mole recovered).

The distillation residue was cooled to 75° C. and semicarbazide free base was extracted with $H_2O$ (150 ml). The aqueous solution was filtered (25° C.) and the filter cake (hydrazodicarbonamide, weight 6.3 grams, 0.053 mole) washed with $H_2O$ (50 ml). Titration of the combined aqueous extract (weight 523.8 grams) with 0.15 N potassium iodate showed 57.2 percent semicarbazide free base (299.6 grams, 3.995 moles).

A slurry of semicarbazide hydrochloride was prepared in-situ by addition of 32 percent hydrochloric acid (477 grams, 4.18 moles) to the aqueous semicarbazide free base (weight 487.1 grams) at 16°–28° C.

Ninety percent formic acid (10.45 moles, 535 grams) was added and the slurry heated at 106°–109° C. for four hours. Hydrogen chloride evolved during this cyclization was collected in 20 percent sodium hydroxide. A formic acid-$H_2O$ azeotrope (890 grams) and hydrogen chloride were distilled at 110°–125° C. and water (160 ml) was added to remove residual formic acid as the $H_2O$-azeotrope (104 grams).

The mother liquor was cooled to 10° C. and siphoned (weight 167.5 grams). Crude 1,2,4-triazol-5-one was recrystallized from water (760 ml, 90°–95° C.), cooled to 10° C., and the supernatant liquid siphoned (weight 896 grams). 1,2,4-Triazol-5-one was filtered and the filter cake rinsed with $H_2O$ (10° C.). The 1,2,4-triazol-5-one product crystals weighed 196.0 grams (2.31 moles; 55.2 percent yield based on $N_2H_4$), had a melting point of 235°–238° C., and assayed 0.27 percent $Cl^-$. The filtrate (254 grams) was recovered.

A second recrystallization from $H_2O$ (630 ml, 90°–95° C.), followed by additional $H_2O$ (210 ml) for transfer gave 157.4 grams of vacuum-dried (50° C.) 1,2,4-triazol-5-one (1.85 moles, 44.3 percent yield), m.p. 236.5°–8° C. (0.03 percent $Cl^-$). The product purity was 99.8 percent (HPLC). The filtrate and aqueous wash (weight 303 grams) were recovered.

EXAMPLE 2

A slurry of aqueous semicarbazide.HCl, prepared using the same quantities of 64 percent hydrazine and urea and the method as described in Example 1, was reacted with 90 percent formic acid (10.45 moles, 535 grams) at 106°–109° C. for four hours. A formic acid-$H_2O$ azeotrope and HCl were stripped at 110°–125° C. (902 grams).

The following process streams from Example 1 were successively added to strip residual formic acid from the reaction mixture at 111°–118° C.; mother liquor (167.5 grams); first recrystallization liquor (896 grams); aqueous wash of first filter cake (254 grams); second recrystallization liquor (527 grams); and aqueous wash of second filter cake (303 grams). A total of 1777 grams of distillate was collected. The reaction slurry was cooled to 10° C. and the mother liquor (250 grams) was siphoned. Crude 1,2,4-triazol-5-one crystals were recrystallized from $H_2O$ (760 ml) at 90°–95° C. After cooling to 10° C., the supernatant liquid was siphoned (857 grams) and the product recrystallized again from 630 ml of $H_2O$ (630 ml). The supernatant liquor (750 grams) was siphoned. Purified product crystals were slurried with $H_2O$ (210 ml) at 10° C., filtered and vacuum-dried at 50° C. to give 270 grams of 1,2,4-triazol-5-one (3.18 moles, 76.1 percent yield), m.p. 237°–239° C.; assay 0.21 percent $Cl^-$. The product assay was 98.9 percent (HPLC). The aqueous cake wash (263 grams) was recovered.

EXAMPLE 3

Urea (271.3 grams, 4.514 moles) and 64 percent hydrazine (209 grams, 4.18 moles) were heated at 110°–111° C. for two hours. Unreacted $N_2H_4$ was vacuum-stripped (weight 87.9 grams, 7.4 percent $N_2H_4$, 0.32 mole). The distillation residue was cooled to 75° C., solubilized with $H_2O$ (150 ml), filtered at 25° C., and the filter cake washed with $H_2O$ (50 ml) and dried (hydrazodicarbonamide 6.4 grams, 0.054 mole). A slurry of semicarbazide hydrochloride was prepared by addition of 32 percent muriatic acid (477 grams, 4.18 moles) to the filtrate (weight 506.1 grams).

Ninety percent formic acid (10.45 moles, 535 grams) was added to the slurry of aqueous semicarbazide hydrochloride and the reaction mixture heated at 107° C. for four hours. A formic acid-$H_2O$ azeotrope and HCl were distilled. Water (160 ml) was added to the distillation residue to remove residual formic acid as the $H_2O$-azeotrope (95.4 grams).

After cooling to 10° C., the product precipitated and mother liquor was siphoned (weight 209.4 grams). Crude 1,2,4-triazol-5-one product crystals were recrystallized from $H_2O$ (760 ml) at 90°–95° C., cooled to 10° C., and the supernatant liquid siphoned (weight 924 grams). The product was recrystallized again from $H_2O$ (630 ml) at 90°–95° C.. The supernatant liquor (10° C.) was siphoned, the purified product was slurried with $H_2O$ (210 ml) at 10° C., filtered and vacuum-dried at 50° C. to give 160.8 grams of 1,2,4-triazol-5-one (1.89 moles, 45.3 percent yield based on $N_2H_4$ charged), m.p. 235°–237° C. (0.06 percent $Cl^-$). The second recrystallization liquor (660 grams) and aqueous cake wash (244 grams) were recovered.

EXAMPLE 4

A slurry of aqueous semicarbazide.HCl was prepared using the same quantities of urea and 64 percent $N_2H_4$ and the method of Example 3. The slurry was reacted with 90 percent formic acid (10.45 moles, 535 grams) at 106°–109° C. for four hours and a formic acid-$H_2O$ azeotrope and HCl stripped from the reaction mixture at 109°–125° C. (weight 898 grams).

The following process streams from Example 3 were successively added to strip residual formic acid from the reaction mixture at 110°–118° C.; mother liquor (209.4 grams), first recrystallization liquor (924 grams), second recrystallization liquor (660 grams) and aqueous cake wash (244 grams). A total of 1566 grams of distillate was collected. The mother liquor (10° C.) was siphoned (weight 408 grams) and crude 1,2,4-triazol-5-one was recrystallized from $H_2O$ (760 ml) at 90°–95° C. The supernatant liquid, cooled to 10° C. was siphoned (weight 950 grams) and the product recrystallized again from $H_2O$ (760 ml). The purified product was slurried with $H_2O$ (210 ml) at 10° C., filtered and vacuum-dried at 50° C. to give 264 grams of 1,2,4-triazol-5-one (3.11 moles, 74.4 percent yield based on N₂H₄ charged), m.p. 236°-238° C. (0.10 percent Cl⁻).

EXAMPLE 5

Aqueous semicarbazide free base feedstock (523.8 grams) was prepared from 64 percent N₂H₄ (4.18 moles) and urea (4.17 moles) by the method of Example 1. Thirty-seven percent hydrochloric acid (205.6 grams, 2.08 moles) and 90 percent formic acid (533.3 grams, 10.44 moles) were successively added to the aqueous semicarbazide free base. The mixture was heated to 107°-110° C. for four hours; a formic acid-H₂O azeotrope distilled (610.5 grams), followed by H₂O addition (160 ml) and resumption of stripping (107 grams). After cooling to 10° C., the mother liquor was siphoned (307 grams). The crude 1,2,4-triazol-5-one was recrystallized from H₂O (760 ml). After cooling to 10° C., the supernatant liquid was siphoned (807 grams) and the product was slurried with an additional 210 ml H₂O (10° C.), filtered, and vacuum-dried to give 168.5 grams of 1,2,4-triazol-5-one (1.98 moles, 47.4 percent yield based on N₂H₄ charged), m.p. 236.5°-8° C. (Cl⁻, 0.22 percent).

EXAMPLE 6

Aqueous semicarbazide free base feedstock (523.8 grams) was prepared from 64 percent N₂H₄ (4.18 moles) and urea (4.17 moles) by the method of Example 1. Ninety-eight percent sulfuric acid (99.8 grams, 0.998 mole) and 90 percent formic acid (510.6 grams, 9.99 moles) were successively added to the aqueous semicarbazide free base. After reflux at 108°-110° C. for four hours, a formic acid/H₂O azeotrope was stripped, H₂O (160 ml) was added to the concentrate and stripping resumed at 118°-125° C. to give 595 grams of combined distillate. The reaction mixture was cooled to 10° C. and the mother liquor was siphoned (58 grams). Crude 1,2,4-triazol-5-one was recrystallized from H₂O (725 ml), the supernatant liquid was siphoned (930 grams), and 200 ml H₂O was added for product filtration. Vacuum-drying gave 152.6 grams of 1,2,4-triazol-5-one (1.80 moles, 43.1 percent yield based on N₂H₄ charged), m.p. 234°-236° C. (Cl⁻, 0.02 percent).

What is claimed is:

1. A process for producing 1,2,4-triazol-5-one which comprises reacting an aqueous hydrazine solution with urea to form a reaction mixture of semicarbazide and ammonia, concentrating the reaction mixture, adding an aqueous solution of a mineral acid to form a slurry of a salt of semicarbazide, admixing a formic acid compound with the slurry, and heating the slurry to produce 1,2,4-triazol-5-one.

2. The process of claim 1 wherein said aqueous hydrazine solution is hydrazine hydrate.

3. The process of claim 2 in which the molar ratio of hydrazine to urea is from about 0.9:1 to about 1.2:1.

4. The process of claim 3 in which the reaction of the aqueous hydrazine solution with the urea is at a temperature of from about 80° C. to about 130° C.

5. The process of claim 1 in which the concentrated reaction mixture is extracted with an aqueous solution to form a slurry of insolubles in a solution of a semicarbazide free base.

6. The process of claim 5 in which the insolubles are separated from the solution of a semicarbazide free base.

7. The process of claim 1 in which the aqueous solution of mineral acid is hydrochloric acid, sulfuric acid, and mixtures thereof.

8. The process of claim 1 in which the formic acid compound formylating agent is represented by the formula:

$$HCZ \qquad (I)$$

wherein
Z represents O₂H, O₂R″, (OR″)₃, O₂M, ONH₂, or (NHCHO)₃, in which
R″ represents a lower alkyl group, and
M represents an alkali metal.

9. The process of claim 8 in which the formic acid compound formylating agent is selected from the group consisting of formic acid, formic acid esters of a lower alcohol having 1 to about 6 carbon atoms, and orthoformic acid esters of a lower alcohol having 1 to about 6 carbon atoms.

10. The process of claim 4 in which a reaction mixture comprising 1,2,4,-triazol-5-one is distilled to separate a first distillate comprising the formic acid compound from a first mother liquor.

11. The process of claim 10 in which crystals of 1,2,4-triazol-5-one are precipitated from the first mother liquor.

12. The process of claim 11 in which the crystals of 1,2,4-triazol-5-one are recrystallized in an aqueous solution and separated from a second mother liquor.

13. The process of claim 7 in which the aqueous solution of mineral acid is hydrochloric acid.

14. The process of claim 11 in which the crystals of 1,2,4-triazol-5-one are separated from the first mother liquor.

15. The process of claim 12 in which the second mother liquor is returned to the slurry of 1,2,4-triazol-5-one.

* * * * *